United States Patent [19]

Konishi et al.

[11] 4,299,827
[45] Nov. 10, 1981

[54] O-ETHYL S-N-PROPYL O-[4-METHYLTHIO(SULFINYL)(SULFONYL)-2(3)-METHOXYPHENYL] PHOSPHOROTHIOLATES AS PESTICIDES

[75] Inventors: Kazuo Konishi, Takatsuki; Yasuo Sato, Kyoto, both of Japan

[73] Assignee: Takeda Chemical Industries, Ltd., Osaka, Japan

[21] Appl. No.: 136,483

[22] Filed: Apr. 2, 1980

[30] Foreign Application Priority Data

Apr. 3, 1979 [JP] Japan .................. 54/40643

[51] Int. Cl.$^3$ ............... A01N 57/14; C07F 9/165
[52] U.S. Cl. ...................... 424/216; 260/949
[58] Field of Search .............. 260/949; 424/216

[56] References Cited

U.S. PATENT DOCUMENTS

| | | | |
|---|---|---|---|
| 3,444,274 | 5/1969 | Schrader | 260/949 |
| 3,792,132 | 2/1974 | Bernhart | 260/949 |
| 3,839,511 | 10/1974 | Kishino et al. | 260/949 |
| 3,917,752 | 11/1975 | Drabek et al. | 260/949 |

FOREIGN PATENT DOCUMENTS

| | | | |
|---|---|---|---|
| 41-11880 | 6/1966 | Japan | 260/949 |
| 1295418 | 11/1972 | United Kingdom | 260/949 |

*Primary Examiner*—Anton H. Sutto
*Attorney, Agent, or Firm*—Wenderoth, Lind & Ponack

[57] ABSTRACT

Organophosphates of the formula:

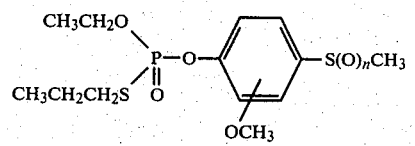

wherein n means zero or an integer of 1 or 2, are new compounds having very good pesticidal activities against insects, mites, ticks and other pests without substantial toxicity to warm-blooded animals, fish and plants.

9 Claims, No Drawings

O-ETHYL S-N-PROPYL O-[4-METHYLTHIO(SULFINYL)(SULFONYL)-2(3)-METHOXYPHENYL] PHOSPHOROTHIOLATES AS PESTICIDES

This invention relates to novel pesticidally active organophosphates, methods for the preparation thereof and pesticidal compositions containing the same. More particularly, the invention relates to an organophosphate having the formula:

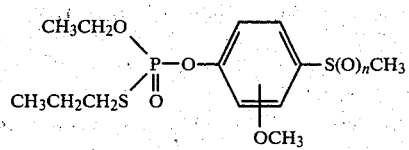     (I)

wherein n means zero or an integer of 1 or 2, methods for the preparation of the organophosphate (I) and a pesticidal composition containing said organophosphate (I).

Various types of insecticides, of which the organophosphate-type are the most important, have been produced for the purposes of increasing food production and ensuring better sanitation. The use of those insecticides over many years has, however, brought forth several negative or undesirable results, as well as the beneficial effects, the negative aspects being the untoward effects on man and animals and on the environment, which have brought serious social problems. On the other hand, the common and continued use of insecticides having similar structures has caused the target insects, mites, ticks and other pests to develop resistance and tolerance to such insecticides and, hence, a considerable decrease of the efficacy of the existing insecticides, thus presenting very unfavorable situations. The situation prompted the urgent need for development of new pesticides which would be safer and more effective against the pests which have acquired multiple cross-resistance to the existing pesticides.

In order to fulfill the above need, the present inventors conducted intensive research. The research led them to the discovery that new organophosphates represented by the formula (I), which are of a type of asymmetric phosphates and differentiate themselves from any of the conventional groups of insecticidally active organophosphates, have properties which are beneficial in solving the above-mentioned problems. The present invention is predicated on the above discovery.

Referring, now, to the above formula (I), a dominant characteristic of the compounds is that a single methoxyl group occurs in the 2- or 3-position (i.e. the ortho- or meta-position) of the benzene ring with respect to the group

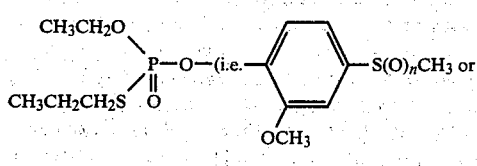

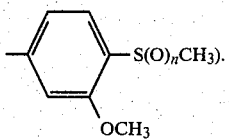

Therefore, the compounds (I) are characterized in that their basic structure may be regarded as a derivative of catechol or resorcinol. The symbol n means zero or an integer of 1 or 2. The group S(O)$_n$CH$_3$ means methylthio group when n is 0, methylsulfinyl group when n is 1, and methylsulfonyl group when n is 2.

It is also one of the characteristics of the compounds (I) of this invention that such sulfur-containing substituents [S(O)$_n$CH$_3$] may occur only in the 4-position (i.e. the para-position) of the benzene ring with respect to the group

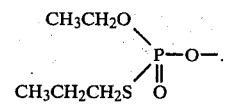

Among thus characterized compounds (I) as above, preferable ones may be exemplified as follows:
(1) O-Ethyl S-n-propyl O-(4-methylthio-2-methoxyphenyl) phosphorothiolate
(2) O-Ethyl S-n-propyl O-(4-methylthio-3-methoxyphenyl) phosphorothiolate
(3) O-Ethyl S-n-propyl O-(4-methylsulfinyl-2-methoxyphenyl)phosphorothiolate
(4) O-Ethyl S-n-propyl O-(4-methylsulfonyl-2-methoxyphenyl)phosphorothiolate
(5) O-Ethyl S-n-propyl O-(4-methylsulfinyl-3-methoxyphenyl)phosphorothiolate
(6) O-Ethyl S-n-propyl O-(4-methylsulfonyl-3-methoxyphenyl)phosphorothiolate Among these compounds, the first-mentioned two compounds (1) and (2) possess particularly excellent pesticidal actions and can be used as broad-spectrum pesticides against the following harmful insects, mites and ticks.

The organophosphates (I) of this invention are quite effective in the control and eradication of a broad spectrum of injurious insects, mites and ticks and exert excellent effects on the following and other pests. The larvae of *Lepidoptera* which masticate and damage agricultural and horticultural plants, such as *Spodoptera litura, Pluttella xylostella, Pieris rapae crucivora, Chilo suppressalis, Helicoverpa assulta, Leucania separata, Mamestra brassicae, Adoxophyes orana, Cnaphalocrocis medinalis* and *Phthorimaea operculella;* the larvae and adults of Coleoptera such as *Epilachna vigintioctopunctata, Phyllotrepta striolate* and *Oulema oryzae;* the larvae and adults of Orthoptera such as *Locusta migratoria;* the larvae and adults of Hemiptera such as *Scotinophara lurida, Stephanitis nashi, Laodelphax striatellus, Nephotettix cincticeps, Unaspis yannonensis, Aphis glycines, Aphis gossypii;* leaf mites; the larvae and adults of *Tetraychus urticae, Panonychus citri* and *Panonychus ulmi;* the nematodes which are parasitic on roots of plants; and other agricultural and horticultural pests such as *Meloidogyne hapla;* insects which feed on stored crops, such as *Sitophilus zeamais, Tribolium castaneum*, etc.; household pests which feed on wool, leather, paper, etc., such as *Tinea pellionella, Attagenus piceus, Ctenole-*

*pisma villosa*, etc.; and household and animal pests which are harmful to man and livestock directly or indirectly, such as *Culex pipiens, Simulium nacojapi, Musca domestica, Lucilia caesar, Periplaneta fuliginosa, Blattela germanica, Ixodes japonensis, Boophilis microplus,* etc. Furthermore, the compounds (I) of this invention are low in toxicity to warm-blooded animals and have little effects on the environment, e.g. low toxicity to fish and no drug damage to plants, and are active even against the insects, mites and tricks resistant to many of the existing pesticides. Therefore, these compounds (I) can be safely used not only as agricultural pesticides but also as pesticides for horticultural, household, sanitation maintenance and animal husbandry uses.

To apply the pesticidal agent according to this invention, one or more of compounds of the formula (I) are used, depending on the intended use, either directly as they are or after being dissolved or dispersed in a suitable carrier or vehicle (e.g. a solvent) or being admixed with or adsorbed on a suitable solid carrier (e.g. a diluent or volume builder), with or without the addition of an emulsifier, dispersing agent, suspension, spreader, sticker, penetrant, wetting agent, viscosity builder, stabilizer and/or other additives. The application forms that can be adopted thus include oil preparations, emulsions, wettable powders, dusts, granules, tablets, spray-mists, etc.

The appropriate concentration of the active compound (I) in such an emulsion or wettable powder may generally be in the range of about 10 to about 90 percent by weight. In an oil or dust preparation, for instance, about 0.1 to about 10 percent by weight is suitable. Such concentrations are, however, not critical but may be varied according to the intended application. In the case of an emulsion, wettable powder or the like, the preparation can be used after diluting it to a suitable concentration, e.g. 500- to 2000-fold, with water or the like.

As the solvent for use in the pesticidal composition of this invention, there may be mentioned alcohols (e.g. methyl alcohol, ethyl alcohol, ethylene glycol, etc.), ketones (e.g. acetone, methyl ethyl ketone, etc.), ethers (e.g. dioxane, tetrahydrofuran, cellosolve, etc.), aliphatic hydrocarbons (e.g. gasoline, kerosene, machine oil, fuel oil, etc.), aromatic hydrocarbons (benzene, toluene, xylene, solvent naphtha, methylnaphthalene, etc.), organic bases (e.g. pyridine, collidine, etc.), acid amides (e.g. dimethylformamide, etc.), esters (e.g. ethyl acetate, etc.), nitriles (e.g. acetonitrile, etc.) and so on. These solvents may be used alone or as a mixture.

As examples of said diluent and volume builder, there may be mentioned vegetable powders (e.g. soybean flour, tobacco powder, walnut flour, wheat flour, saw dust, etc.), mineral powders (e.g. kaolin, bentonite, acid clay and other clayish materials, talcum powder, pyrophyllite and other talcs, diatomaceous earth, mica powder and other silicas), alumina, silica gel, sulfur powder, activated carbon, calcium phosphate, etc. These materials may be used alone or as a mixture. Surfactants which can be employed by way of a spreader, emulsifier, penetrant, dispersing agent, solubilizer, etc. include, for example, various soaps, higher alcohol sulfate esters, olefin sulfates, sulfonated oil, ethanolamine, higher fatty acid esters, alkylarylsulfonates, quaternary ammonium salts, alkylene oxide surfactants, anhydrosorbitol surfactants, etc. Moreover, casein, gelatin, agar, starch, bentonite, aluminum hydroxide, etc. may further be added.

It is also possible to employ such compositions as supplemented with other insecticides (synthetic and natural insecticides), acaricides, nematocides, fungicides, herbicides, plant growth regulators, synergists, attractants, repellents, perfumes, etc. If desired, various plant nutrients, fertilizers, etc. may also be incorporated or used in admixture with the compositions according to this invention.

The composition containing the compound (I) can be employed to control the above-mentioned insects or mites attacking for example, dry field harvest, such as cabbages, soybeans, maizes, cotton, tobacco, fruit trees of apples, oranges, etc. The composition can also be applied to the inside and outside of cattle barns or poultry houses. The amount of the effective component to be used is usually within the range of from ca. 50 g to ca. 5 kg per ha., preferably from ca. 300 g to ca. 3 kg per ha.

It is also found that by applying a compound of the formula (I) to cotton plants, seed cotton can be profitably increased in yield. The amount of effective component, types of preparations and methods of application thereof are similar to those described hereinbefore. As most preferable among those preparations, there may be mentioned an emulsion.

The compound (I) according to this invention can be produced, for example, by reacting a phenol compound of the formula:

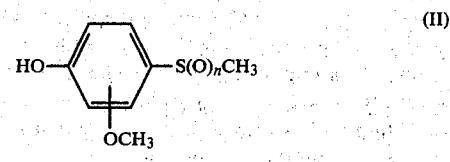

wherein n has the same meaning as defined hereinbefore, with a phosphoric acid halide of the formula:

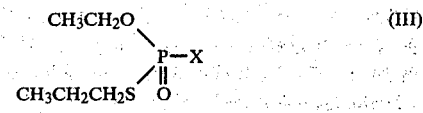

wherein X means a halogen atom such as Cl, Br, etc.

This reaction of the phenol compound (II) with the phosphoric acid halide (III) is generally conducted with advantage in an organic solvent, which may be of any type, only if it does not interfere with the reaction. Aprotic solvents, however, are most desirable. Thus, for example, there may be employed, either alone or as a mixture, such solvents as halogenated aliphatic hydrocarbons (e.g. chloroform, methylene chloride, ethylene chloride, etc.), aromatic hydrocarbons (e.g. benzene, toluene, xylene, chlorobenzene, etc.), esters (e.g. ethyl acetate, butyl acetate, etc.), ketones (e.g. acetone, methyl ethyl ketone, methyl isobutyl ketone, etc.), ethers (e.g. diethylether, tetrahydrofuran, dioxane, dimethoxyethane, etc.), amides and nitriles (dimethylformamide, N-methylpyrrolidone, acetonitrile, etc.) and compounds containing sulfur or phosphorus (e.g. dimethylsulfoxide, tetramethylenesulfone, hexamethylphosphorotriamide, etc.). These solvents may be employed alone or as a suitable mixture of two or more species. If desired, however, water or alcohol (e.g. methanol, ethanol, i-propanol, n-butanol, methylcellosolve, etc.) may also be employed and there are cases in which the presence of a small amount of water or alcohol is conducive to a faster reaction. The reaction is advantageously carried out in the presence of an acid acceptor.

The acid acceptor is usually an organic or inorganic base. Preferred examples of the organic base include tertiary amines such as triethylamine, tributylamine, triethylenediamine, 1,4-diazabicyclo[2,2,2]octane, 1,8-diazabicyclo[5,4,0]-7-undecene, 1,5-diazabicyclo[4,3,0]-5-nonene, dimethylaniline, diethylaniline, pyridine, 4-dimethylaminopyridine, S-collidine, etc. Such as organic base may be employed in a large amount so that it will act as the reaction solvent as well. As examples of said inorganic base, there may be mentioned the oxides, hydroxides, carbonates, bicarbonates and alkoxides of alkali metals or alkaline earth metals. Aside from the above, basic ion exchange resins may also be employed in certain cases. Such as acid acceptor may be added to the reaction mixture or, alternatively, it may be first reacted with the phenol compound (II) to obtain a phenolate and the latter be reacted with the phosphoric acid halide (III).

Since, generally, this reaction proceeds smoothly with a slight evolution of heat, the reaction system need not necessarily be heated if conducted under vigorous stirring. If, however, it is desired to complete the reaction within a short period of time, it may be necessary to conduct the reaction at an elevated temperature. The reaction temperature is usually in the range of from room temperature (10° C.) to about 100° C., although a still higher temperature may be needed in certain cases. If, on the contrary, it is difficult to control the reaction due to an evolution of intense heat, the reaction will have to be conducted under cooling to from about 10° C. to about −20° C. in order to retard the reaction. While the reaction is usually carried out at atmospheric pressure, it may be conducted at elevated pressure in a sealed reaction vessel. The reaction usually goes to completion within a few hours but, in certain cases, only after a few days. This reaction does not require a catalytic additive but there are cases in which the addition of a small amount of copper powder (in acetone or the like), potassium iodide (in acetone or the like), crown ether (in acetonitrile or the like) or a phase-transfer catalyst (in water-toluene or the like) may prove effective.

The organophosphates of the formula (I) can be produced with the highest efficiency by the above-described reaction method, but they can also be produced by other alternative methods. Some of such alternative methods will be shown below by way of chemical reaction formulas.

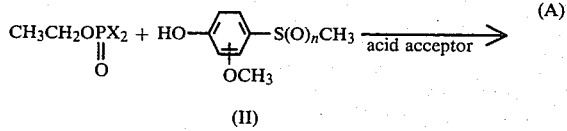

(A)

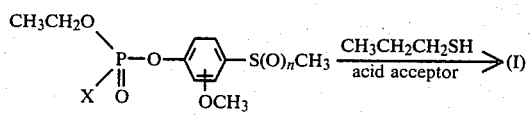

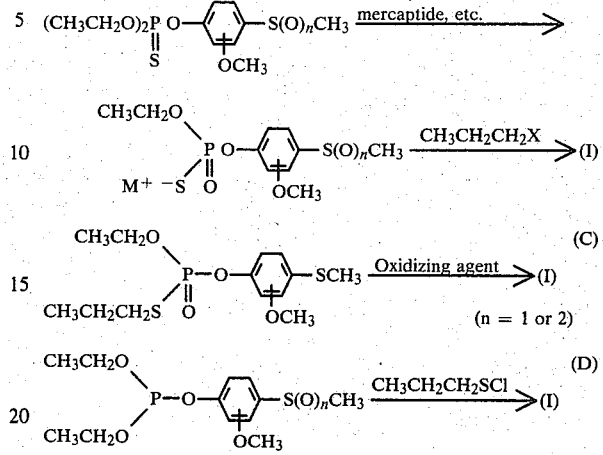

In the above formulas, n and X are as defined hereinbefore; M means a hydrogen atom, alkali metal, an ammonium group, etc.

The above reactions (A) to (D) can be conducted by the known methods or analogous methods, e.g. in accordance with the procedures described in Japanese Published examined patent application No. 49-24656, No. 48-26221, No. 51-20506, and No. 52-86, and British Pat. No. 1,295,418, for instance.

The organophosphates (I) which can be obtained by the above methods are normally oily products which, at room temperature, are colorless to slightly yellowish, have a faint odor and are slightly viscous, being highly soluble in most organic solvents excepting petroleum-based aliphatic hydrocarbons.

Therefore, after the reaction, the product compound (I) of nearly absolute or high purity can be obtained simply by washing the reaction mixture, in a water-immiscible organic solvent, with a dilute aqueous solution of alkali carbonate or alkali hydroxide and water, dehydrating it and concentrating the same. If desired, the product can be further purified by column chromatography or distillation in high vacuum. Among the starting compounds, the 4-methylthio-2- or 3-methoxy-phenol compounds of the formula (II) can be easily obtained, for example by reacting a 2- or 3-methoxy-phenol compound with a suitable sulfenylating agent (e.g. methyl sulfide, methyl disulfide, methyl sulfoxide, methyl sulfenyl halide, methylthiol sulfonate, etc.) in the presence of a suitable catalyst (e.g. halogen, inorganic acid, inorganic or organic acid halide, inorganic or organic acid anhydride, Lewis acid, inorganic or organic base, etc.). The same compounds can also be easily obtained by the selective methylation of the mercapto group introduced into the 4-position of a 2- or 3-methoxy-phenol compound (para-position) by diazotization reaction with a suitable methylating agent (e.g. methyl halide, methyl sulfate ester, methyl sulfonate ester, etc.).

The same compounds can also be obtained by permitting alkali hydroxide or alkali cyanide to act upon the corresponding 4-thiocyanatophenols [Konishi: Annual Reports of the Takeda Research Laboratory 24, 233 (1965)] in methanol. Furthermore, the 4-methylsulfinyl-phenol (n=1) and 4-methylsulfonylphenol (n=2) compounds can be easily obtained by oxidizing the corresponding 4-methylthiophenol (n=0) compounds with a suitable oxidizing agent (e.g. hydrogen peroxide, halogen, inorganic or organic peracid, nitric acid, potassium permanganate, sodium metaperiodate, an N-halogenoamide, an imide compound, etc.).

Among the phenol compounds of the formula (II), 4-methylthio-3-methoxyphenol is the compound which has been described in the literature and has been synthesized by the method referred to hereinbefore [B. S. Farah and E. E. Gilbert: Journal of Organic Chemistry 28, 2807 (1963); S. Ukai and K. Hirose; Chemical and Pharmaceutical Bulletin 16, 202 (1968)]. However, the other compounds have not been described in the literature, within the best of the present inventors' knowledge. Therefore, physical constants will be given below for some of the novel phenol compounds (II) which have been synthesized by the inventors by the above-described methods or by methods analogous thereto.

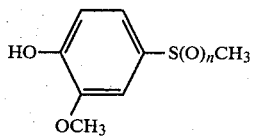

| n | Constants |
|---|---|
| 0 | b.p. 124–126° C./4mmHg, m.p.50° C. |
| 1 | m.p. 127–129° C. |
| 2 | m.p. 149–151° C. |

(b.p. = boiling point, m.p. = melting point)

The phosphoric acid halides of the formula (III) are compounds which have been described in the literature [Japanese Published examined patent application No. 52-86] and can also be produced easily by methods analogous to the methods described in other literatures [c.f. A. E. Lippman: Journal of Organic Chemistry 30, 3217(1965)].

The following examples, reference examples and test example are intended to illustrate this invention in further detail and should by no means be construed to delimit the scope of the invention. In this specification, the following abbreviations are used: milliliter=ml, liter=l, gram=g, kilogram=kg, centimeter=cm, boiling point=b.p., melting point=m.p., percent=%, parts per million=ppm, decomposition=decompn., diameter=dia. And trade name "Tween-20 ®" are products manufactured by Kao Atlas Co., Ltd. in Japan and "Dyne ®" are products manufactured by Takeda Chemical Industries, Ltd. in Japan.

EXAMPLE 1

In 100 ml of toluene is dissolved 6.81 g (0.04 mol) of 4-methylthio-2-methoxyphenol, followed by addition of 5.06 g (0.05 mol) of triethylamine. While this solution is stirred at room temperature, a solution of 8.11 g (0.04 mol) of O-ethyl-S-n-propylthiolophosphoryl chloride is 20 ml of toluene is added slowly and dropwise, whereby triethylamine hydrochloride begins to separate out with a slight elevation of the internal temperature beyond room temperature. After the dropwise addition has been completed, the reaction mixture is further stirred at room temperature for a few hours. The reaction mixture is filtered to remove the crystals and the filtrate is washed with water, a 10% aqueous solution of sodium carbonate, water, 1 N-HCl, water and a saturated aqueous solution of sodium chloride in the order mentioned, followed by dehydration over anhydrous sodium sulfate. This toluene solution is filtered through a thin bed of decolorizing charcoal and the filtrate is concentrated under reduced pressure in a rotary vacuum evaporator. The oily residue is then subjected to a suction force to a constant volume by means of a vacuum pump, whereby O-ethyl S-n-propyl O-(4-methylthio-2-methoxyphenyl)phosphorothiolate (Compound No.(1)) is obtained as a pale yellow oil in quantitative yield (13.92 g). The purity of the organophosphate ester thus obtained is as high as to give a nearly single spot in thin-layer chromatography (silica gel/ether) but it is further purified by silica gel column chromatography (toluene-chloroform). Refractive index $n_D^{20}$ 1.5519; b.p. 176°–179° C./0.2 mmHg. The oral acute toxicity value ($LD_{50}$, mg/kg) obtained with five-week aged, ddY-SLC strain mice (26±2 g) is >300.

EXAMPLE 2

To 100 ml of toluene is added 5.96 g (0.035 mol) of 4-methylthio-3-methoxyphenol, followed by addition of 4.55 g (0.045 mol) of triethylamine, whereupon a homogeneous solution is obtained. While this solution is stirred, a solution of 7.09 g (0.035 mol) of O-ethyl S-n-propylthiolophosphoryl chloride in 20 ml of toluene is slowly added dropwise. Thereafter, the reaction mixture is treated as in Example 1 to obtain O-ethyl S-n-propyl O-(4-methylthio-3-methoxyphenyl)phosphorothiolate (Compound No. (2)) as a light-yellow oil in quantitative yield (11.87 g). Refractive index $n_D^{20}$1.5521. The oral acute toxicity value ($LD_{50}$, mg/kg) obtained with five-week aged, ddY-SLC strain mice (26±2 g) is 300.

EXAMPLE 3

The structures, appearances and physical constants of the compounds of this invention, No.3 and No.4, as produced by the same procedures as Example 1 are given below.

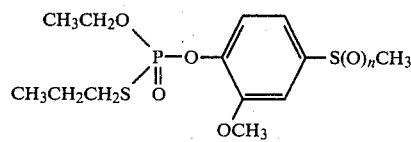

| Compound No. | n | Appearance | Refractive index, $n_D^{20}$ |
|---|---|---|---|
| (3) | 1 | Light yellow oil | 1.5394 |
| (4) | 2 | Light yellow oil | 1.5290 |

EXAMPLE 4

A dust comprising a mixture of 2 parts of Compound No.(1) and 98 parts of talc.

EXAMPLE 5

A solution comprising 25 parts of Compound No.(2), 20 parts of Tween-20 ® and 55 parts of acetone.

EXAMPLE 6

An emulsion comprising a mixture of 50 parts of Compound No.(2), 25 parts of polyoxyethylene diphenyl ether and 25 parts of xylene.

EXAMPLE 7

A wettable powder comprising a milled mixture of 20 parts of Compound No. (2), 4 parts of sodium ligninsulfonate, 4 parts of polyoxyethylene alkylaryl ether, 3 parts of white carbon and 69 parts of clay.

EXAMPLE 8

A granular preparation comprising 5 parts of Compound No.(1) and 95 parts of bentonite as kneaded with a small amount of water and granulated.

REFERENCE EXAMPLE 1

Production of 4-methylthio-2-methoxyphenol

2-Methoxyphenol (25 g, 0.2 mol) and dimethylsulfoxide (16 g, 0.2 mol) are admixed, and under ice-cooling at a temperature not exceeding 10° C. and stirring, the mixture is saturated with dry hydrogen chloride gas. The mixture is further stirred for an hour at room temperature, at the end of which time a small amount of methanol is added to the viscous reaction mixture. The resulting white crystals are collected by filtration, washed with ether and dried under reduced pressure in a desiccator over potassium hydroxide. Yield 34 g (76%); m.p. 135° C. (decompn.)

A Claisen flask is filled with 32.5 g (0.15 mol) of the above crystals and heated to 120°–130° C., whereby the crystals begin to decompose with the evolution of methyl chloride gas. After the gas has ceased to evolve, the residual oil is purified by vacuum distillation. By the above procedure is obtained the desired phenol compound as a faintly colored viscous oil. Yield 22.5 g (88%); b.p.124°–126° C./4 mmHg.

The oil crystallizes on standing and a portion of the crystals are taken and recrystallized from dilute methanol. This procedure yields colorless needles melting at 50° C.

The crystals are in agreement with the compound (b.p. 124°–126° C./4 mmHg) obtained by the selective methylation of the mercapto group of a 4-mercapto-2-methoxyphenol (b.p. 100° C./4 mmHg) from a diazotization process with dimethyl sulfate in the conventional manner.

REFERENCE EXAMPLE 2

Production of 4-methylthio3-methoxyphenol

In 300 ml of methanol is dissolved 14.25 g (0.08 mol) of 4-thiocyanato-3-methoxyphenol, and under ice-cooling and stirring, 7.84 g (0.16 mol) of sodium cyanide is added in portions. After the addition has been completed, the mixture is further stirred. It is then allowed to stand at room temperature overnight and boiled under reflux for a few hours. After the addition of a small amount of decolorizing charcoal, the reaction mixture is filtered and the filtrate is concentrated under reduced pressure in a rotary vacuum evaporator. The residual viscous oil is dissolved in a small amount of water, made acidic with hydrochloric acid and extracted with 3 portions of benzene. The benzene solution is washed with water, dehydrated over anhydrous sodium sulfate and concentrated to dryness under reduced pressure in a rotary vacuum evaporator. The crude crystalline residue is recrystallized from a mixture of cyclohexane and benzene. Yield 9.60 g (70%). With use of decolorizing charcoal, the crystals are further recrystallized from the same solvent system to obtain colorless needles melting at 96°–98° C.

The above crystals are in agreement with the compound (m.p.97°–99° C.) obtained by repeating the same procedure as above but using 3-methoxyphenol in place of 2-methoxyphenol in Reference Example 1.

TEST EXAMPLE

The relative insecticidal effects of the compounds No. (1) to No.(4) of this invention and the following known compounds (a), (b), (c) and (d) having structures similar thereto on *Spodoptera litura, Pluttella xylostella, Mamestra brassicae* and *Epilachna vigintioctopunctata* were tested (in duplicate) by the following procedures.

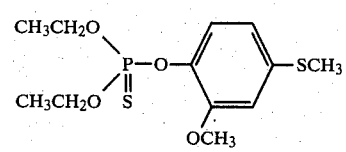

Compound (a):

[Compound (4) in Japanese Published examined patent application No. 41-11880]

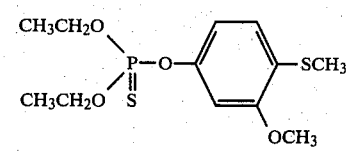

Compound (b):

[Compound (5) in Japanese Published examined patent application No. 41-11880]

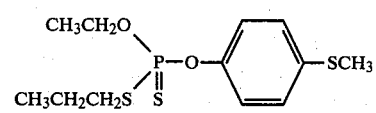

Compound (c):

[Example 2 in British Pat. No. 1,295,418]

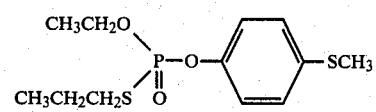

Compound (d):

[Compound No.1 in Japanese Published examined patent application No. 48-26221]

TEST PROCEDURE USING *SPODOPTERA LITURA*

Each test compound was formulated into an emulsion according to the formula mentioned in Example 6 and diluted with water containing a sticker (Dyne ®, ca. 0.03%) to a concentration of 100 ppm. Soybean seedlings (10 days after germination) cultivated with ater in a plastic cup were sprayed with 20 ml of the solution containing 100 ppm of each test compound in a spray chamber using a spray gun (nozzle pressure 1 kg/cm$^2$). The sprayed seedlings were stored in an air-conditioned greenhouse. Six days after the spraying, 2 leaves were excised and each leaf was put in a plastic cup (6 cm in dia. 4 cm deep), into which ten 2nd instar-larvae of *Spodoptera litura* were then released. After the release of larvae, the cups were placed in a room (25° C.), and the larvae mortality was investigated after 48 hours.

TEST PROCEDURE USING PLUTTELLA XYLOSTELLA

Using 20 ml of the solution containing 200 ppm of each test compound as prepared according to the same procedure used for *Spodoptera litura*, radish plants (20 days after germination) cultivated in the soil in plastic cups were sprayed by the same procedure as that used for *Spodoptera litura*. One day after the spraying, two radish leaves were excised and each leaf was placed in a plastic cup, into which ten 2nd to 3rd instar-larvae of *Pluttella xylostella* were released. After the release of larvae, the cups were placed in a room (25° C.) and the larvae mortality was investigated after 48 hours.

TEST PROCEDURE USING MAMESTRA BRASSICAE

By the same procedure described for *Spodoptera litura*, soybean seedlings were sprayed with a solution containing the same concentration (100 ppm) of each test compound as prepared similarly as for *Spodoptera litura*. One day after the spraying, two soybean leaves were excised and each leaf was placed in a plastic cup, into which ten 3rd instar-larvae of *Mamestra brassicae* were then released. After the release of larvae, the cups were placed in a room (25° C.) and the larvae mortality was investigated after 48 hours.

TEST PROCEDURE USING EPILACHNA VIGINTIOCTOPUNCTATA

Each test compound was formulated into a solution according to the formula mentioned in Example 5 and diluted with water containing a sticker (Dyne®, 0.02%) to a concentration of 500 ppm. Slices of white potato were immersed in the diluted solution for 10 seconds and, after drying in the air, the slices were placed in a petri dish (9 cm in dia.), into which ten 3rd instar-larvae of *Epilachna vigintioctopunctata* were then released. After the release of larvae, the dish was placed in a room (25° C.), and the larvae mortality was investigated after 48 hours.

Based on the results of each test, the percent survival (%) was calculated by means of the following equation.

$$\frac{\text{No. of test insects} - \text{No. of dead insects}}{\text{No. of test insects}} \times 100 = \text{percent survival (\%)}$$

The percent survival data are given in the following table.

| | Test compound | Test insect | | | |
|---|---|---|---|---|---|
| | | Spodoptera litura | Pluttella xylostella | Mamestra brassicae | Epilachna vigintiocto-punctata |
| Compounds of this invention | 1 | 0 | 0 | 0 | 0 |
| | 2 | 0 | 5 | 0 | 0 |
| | 3 | 20 | 5 | 0 | 0 |
| | 4 | 10 | 10 | 0 | 10 |
| Conventional compounds | a | 100 | 100 | 100 | 0 |
| | b | 100 | 100 | 100 | 100 |
| | c | 20 | 0 | 75 | 20 |
| | d | 5 | 0 | 50 | 0 |

What we claim is:
1. An organophosphate of the formula:

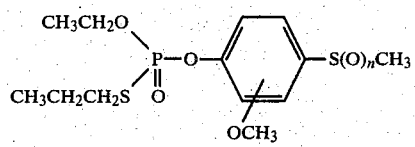

wherein n is zero or an integer of 1 or 2.

2. An organophosphate as claimed in claim 1, wherein n is 0.

3. An organophosphate as claimed in claim 1, wherein the methoxyl group occurs in the 2-position of the benzene ring with respect to the group

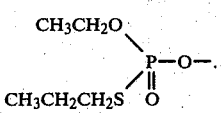

4. An organophosphate as claimed in claim 1, wherein the methoxyl group occurs in the 3-position of the benzene ring with respect to the group

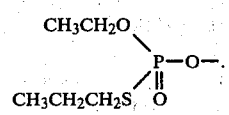

5. An organophosphate as claimed in claim 2, which is O-ethyl S-n-propyl O-(4-methylthio-2-methoxyphenyl)phosphorothiolate.

6. An organophosphate as claimed in claim 2, which is O-ethyl S-n-propyl O-(4-methylthio-3-methoxyphenyl)phosphorothiolate.

7. An organophosphate as claimed in claim 1 or 3, which is O-ethyl S-n-propyl O-(4-methylsulfinyl-2-methoxyphenyl)phosphorothiolate.

8. An organophosphate as claimed in claim 1 or 3, which is O-ethyl S-n-propyl O-(4-methylsulfonyl-2-methoxyphenyl)phosphorothiolate.

9. A pesticidal composition which contains a pesticidally effective amount of at least one organophosphate of the formula:

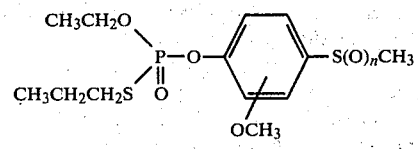

wherein n is zero or an integer of 1 or 2, together with at least one suitable carrier or vehicle.

* * * * *